US00PP36867P2

(12) United States Plant Patent
Davidson

(10) Patent No.: US PP36,867 P2
(45) Date of Patent: Jul. 29, 2025

(54) ***DASIPHORA* PLANT NAMED 'Bailpine'**

(50) Latin Name: *Dasiphora fruiticosa*
Varietal Denomination: Bailpine

(71) Applicant: His Majesty the Kind in the right of Canada as represented by the minister of Agriculture and Agrifood, Saint-Hyacinthe (CA)

(72) Inventor: Campbell G. Davidson, West Hawk Lake (CA)

(73) Assignee: HIS MAJESTY THE KING IN THE RIGHT OF CANADA AS REPRESENTED BY THE MINISTER OF AGRICULTURE AND AGRIFOOD, Saint-Hyacinthe (CA)

( * ) Notice: Subject to any disclaimer, the term of this patent is extended or adjusted under 35 U.S.C. 154(b) by 0 days.

(21) Appl. No.: 18/920,672

(22) Filed: Oct. 18, 2024

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./237
CPC ..... A01H 5/02; A01H 5/00; A01H 6/74
See application file for complete search history.

(56) References Cited

U.S. PATENT DOCUMENTS

PP33,159 P3 * 6/2021 Pineau ..... A01H 5/02
Plt./237

* cited by examiner

*Primary Examiner* — June Hwu
(74) *Attorney, Agent, or Firm* — Penny J. Aguirre

(57) ABSTRACT

A new cultivar of *Dasiphora* plant named 'Bailpine' that is characterized by its compact, mounded form, its tinted with blue-green new foliage and dark green mature foliage, and its double flowers that are bright golden yellow in color.

3 Drawing Sheets

Botanical classification: *Dasiphora fruiticosa.*
Variety denomination: 'Bailpine'.

BACKGROUND OF THE INVENTION

The present invention relates to a new and distinct cultivar of *Dasiphora fruiticosa*. The new cultivar will be referred to hereafter by its cultivar name, 'Bailpine'. 'Bailpine' is a new cultivar of deciduous shrub grown for landscape use.

The new cultivar is the result of a controlled breeding program conducted by the Inventor in Morden, MB, Canada. The intent of the breeding program is to develop new cultivars of *Dasiphora* with double flowers and unique flower colors. 'Bailpine' originated as a seedling that arose from seed planted from open pollination of an unnamed and unpatented plant of *Dasiphora fruiticosa* from the breeders' program designated as No. 98176 in 2000. The male parent is therefore unknown. 'Bailpine' was selected as a single unique plant in July of 2002 from the resulting seedlings.

Asexual propagation of the new cultivar was first accomplished by softwood cuttings by the Inventor in Cottage Grove, MN in July of 2003. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'Bailpine' as a unique cultivar of *Dasiphora.*

1. 'Bailpine' exhibits a compact, mounded form.
2. 'Bailpine' exhibits matte, tinted with blue-green new foliage and dark green mature foliage.
3. 'Bailpine' exhibits double flowers that are bright golden yellow in color.

The female plant of 'Bailpine' differs from 'Bailpine' in having flowers that are light yellow in color with more petals per flower. 'Bailpine' can also be compared to the *Dasiphora* cultivars 'Bailmeringue' (not patented) and 'Goldfinger' (not patented). 'Bailmeringue' is similar to 'Bailpine' in having double flowers and a compact and mounded plant form. 'Bailmeringue' differs from 'Bailpine' in having smaller flowers that are pale yellow in color, and foliage that is light green in color. 'Goldfinger' is similar to 'Bailpine' in having blue-green foliage and a compact and mounded plant form. 'Goldfinger' differs from 'Bailpine' in having single flowers that are darker golden yellow in color.

BRIEF DESCRIPTION OF THE DRAWINGS

The accompanying color photographs illustrate the overall appearance and distinct characteristics of the new *Dasiphora*. The photographs were taken of a 5-year-old plant of 'Bailpine' as grown outdoors in a 2-gallon container in Cottage Grove, Minnesota.

The photograph in FIG. 1 provides a side view of 'Bailpine' in bloom.

Figure 1:
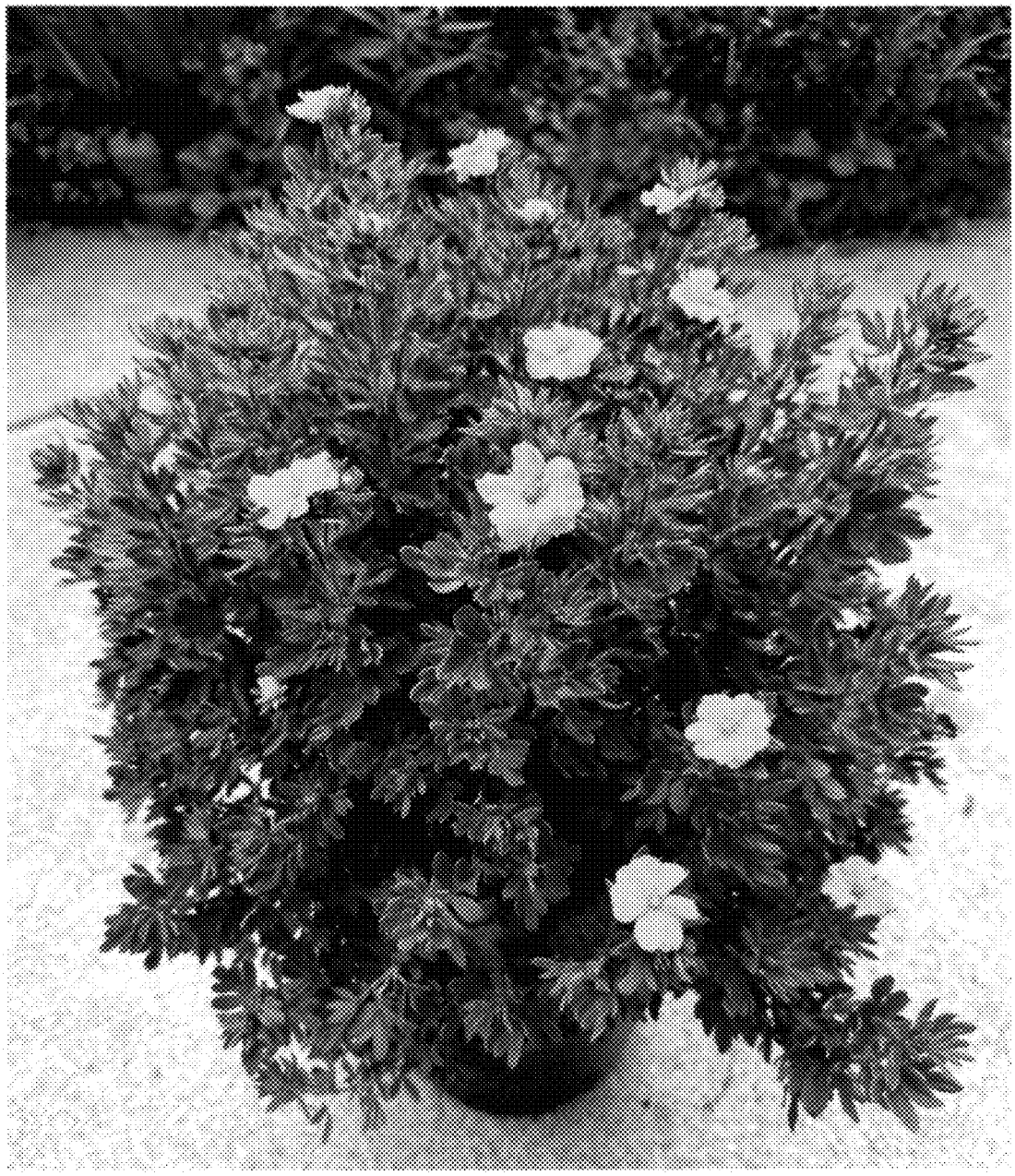
Figure 2:
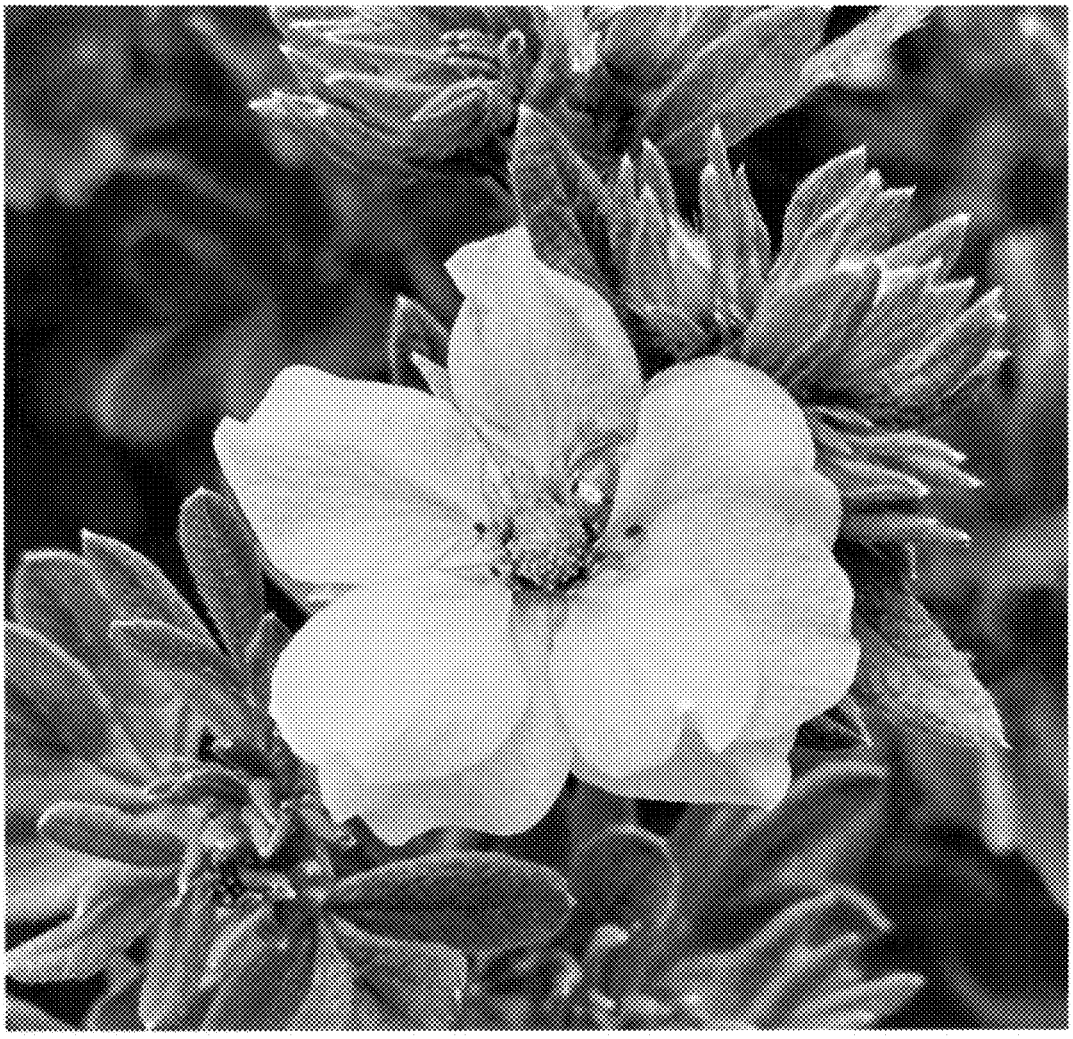

The photograph in FIG. 2 provides a provides a close-up view of a flower of 'Bailpine'.

Figure 3:
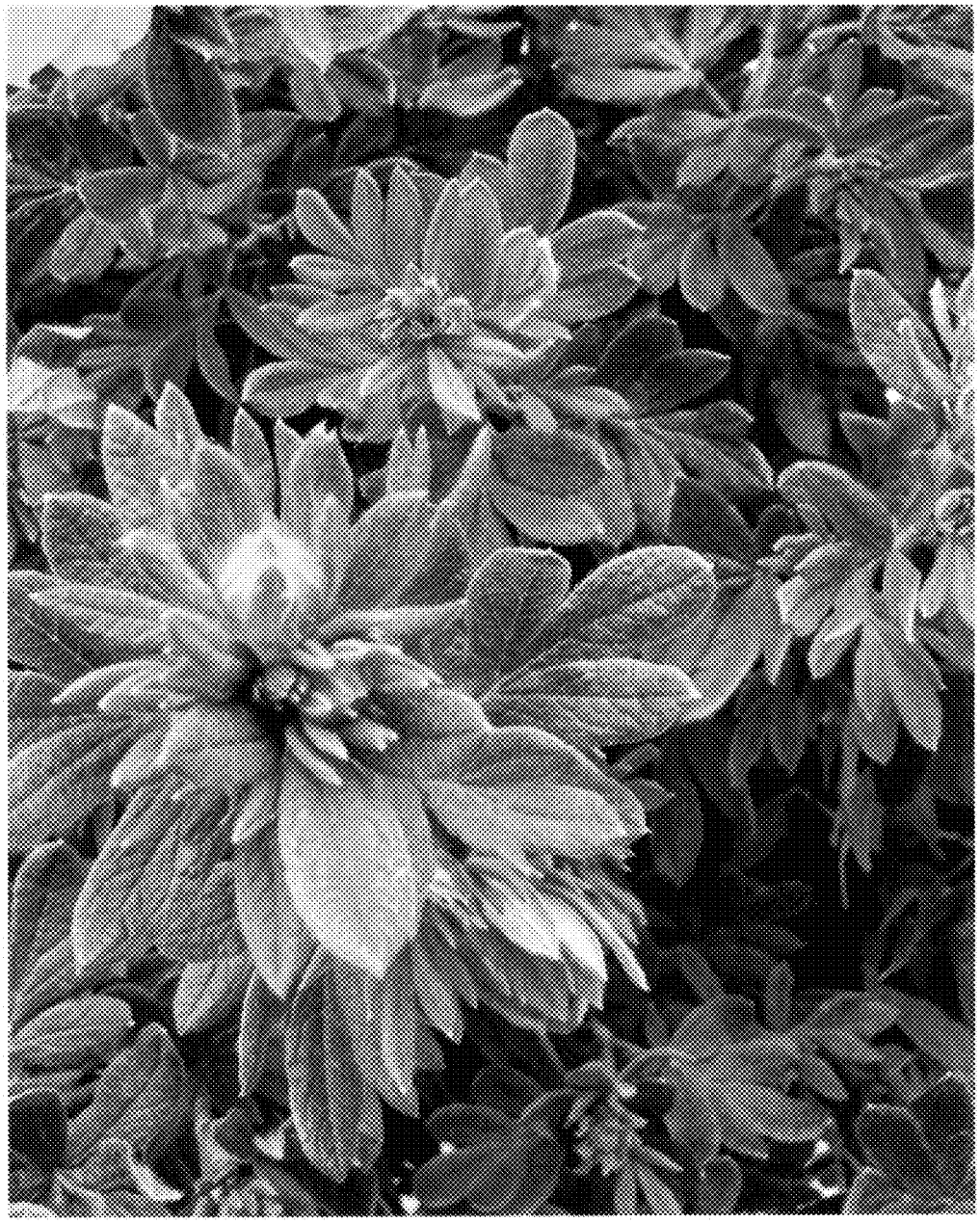

The photograph in FIG. 3 provides a close-up view of the foliage of 'Bailpine'.

The colors in the photographs are as close as possible with the photographic and printing technology utilized and the color values cited in the detailed botanical description accurately describe the colors of the new *Dasiphora*.

DETAILED BOTANICAL DESCRIPTION

The following is a detailed description of 5-year-old plants of 'Bailpine' as grown outdoors in 2-gallon containers in Cottage Grove, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—2 weeks from June and intermittently through September.

*Plant type*.—Deciduous shrub.

*Plant habit*.—Compact, mounded.

*Height and spread*.—An average of 45 cm in height and 51 cm in width as grown in a container, reaches about 91 cm in height and spread as grown in the landscape.

*Hardiness*.—At least in U.S.D.A. Zones 3 to 8.

*Diseases and pests*.—None observed.

*Propagation*.—Softwood cuttings.

*Root description*.—Fine, fibrous, 155C and 200B.

*Growth rate*.—Moderate.

*Root development*.—Cuttings initiate roots in 4 weeks and a fully rooted young plant is produced in 60 days.

Branch description:

*Branch shape*.—Rounded.

*Branch color*.—Young and mature; 142C, flushed with 173A, old; 200A and N200B, and 178A.

*Branch surface texture*.—Young and mature; densely covered with long, fine, soft hairs, up to 2 mm in length, ranges between NN155D in color and matching color of branch surface, old; exfoliating, matte.

*Branching*.—Freely branching, outward to upright.

*Branch size*.—An average of 30 cm in length and 2 mm in diameter.

*Branch quantity*.—Main; 50, lateral; 400.

*Internode length*.—Average of 1 cm.

Foliage description:

*Leaves*.—Compound, alternate arrangement, reniform in shape, an average of 4 cm in length, 3.5 in width, 50 leaves per branch.

*Leaflets*.—7, obovate in shape, rounded apex, truncate base, entire margins, an average of 2 cm in length and 6 mm in width, unlobed, both surfaces matte, both surfaces densely pubescent with tomentose hairs, up to 1.5 mm in length, NN155D in color, color; upper surface 147A with new growth 194A, both mature and immature lower surface 194A.

*Stipules*.—Narrow oblong in shape, both sides smooth and glabrous, matte, 7 mm in length, 2 mm in width, top cleft, base narrow cuneate, color both surfaces; 139A.

*Petioles*.—An average of 6 mm in length and 0.8 mm in diameter, medium strength, color; 143D in color, surface is densely covered with long, fine, soft hairs with a shiny appearance, 0.9 mm in length, NN155D in color.

Inflorescence description:

*Inflorescence type*.—Solitary, terminal and axillary at upper nodes of stems.

*Flower number*.—An average 1 flower and 3 buds per main stem, 400 flowers and buds per plant.

*Flower fragrance*.—None.

*Flower longevity*.—About 5 days, self-cleaning.

*Flower type*.—Single, rotate.

*Flower aspect*.—Upright to slightly outward.

*Flower size*.—An average of 3 cm in diameter and 1 cm in depth.

*Pedicels*.—An average of 1 cm in length, 1 mm in diameter, held vertical, 143D in color, surface is matte, and densely covered with long, fine, soft hairs with a shiny appearance, 1.3 mm in length, NN155D in color.

*Flower buds*.—Spherical in shape, flattened, an average of 5 mm in diameter, 3.5 mm in depth, color; 143A, top lightly flushed with 178A, surface is densely covered with long, fine, soft hairs with a shiny appearance, 2 mm in length, NN155D in color.

*Sepals*.—5, deltoid in shape, entire margins, 1 cm in length, 4 mm in width, acuminate apex, truncate base, both surfaces matte and densely covered with long, fine, soft hairs with a shiny appearance, 1.3 mm in length, NN155D in color, color; both surfaces base 11B, apex 191A, epicalyx; 5-lobed, lanceolate in shape, entire margins, acute apex, an average of 1 cm in length and 4 mm in width, upper and lower surface; 139A in color and very slightly pubescent.

*Petals*.—Average of 15, whorled, orbicular in shape, obtuse apex, cuneate base, margins are entire and slightly undulate, both surfaces are smooth, glabrous, velvety, and matte, color; when opening upper and lower surface a blend of 14A and 6A, when fully open upper surface a blend of 9A and 1A, when fully open lower surface 8A.

*Receptacle*.—Very densely pubescent, 2 mm in depth, 5 mm in diameter, 144A in color.

Reproductive organs:

*Pistils*.—Average of 50, pilose at base, 4 mm in diameter, stigma; very minute, rounded in shape and less than 0.5 mm in diameter, 14A in color, style; average of 1.4 mm in length, color 19A at the top section and NN155D at the mid-section to base, ovary; superior, 2 mm in diameter and depth, 144A in color.

*Stamens*.—18 to 20 per flower, filaments; average of 2 mm in length, color; base 11C, top 11A, anthers; average of 1 mm in length, 0.8 mm in width, oblong in shape, color; center 11A, margins 164A, maturing to 172A and 203A, pollen; low in quantity, 11A in color.

*Fruit and seed*.—Have not been observed to date.

It is claimed:

1. A new and distinct cultivar of *Dasiphora* plant named 'Bailpine' as herein illustrated and described.

* * * * *